July 14, 1964 J. R. VOELLER Plant Pat. 2,422
CHAENOMELES LAGENARIA CLIMBER
Filed June 4, 1962
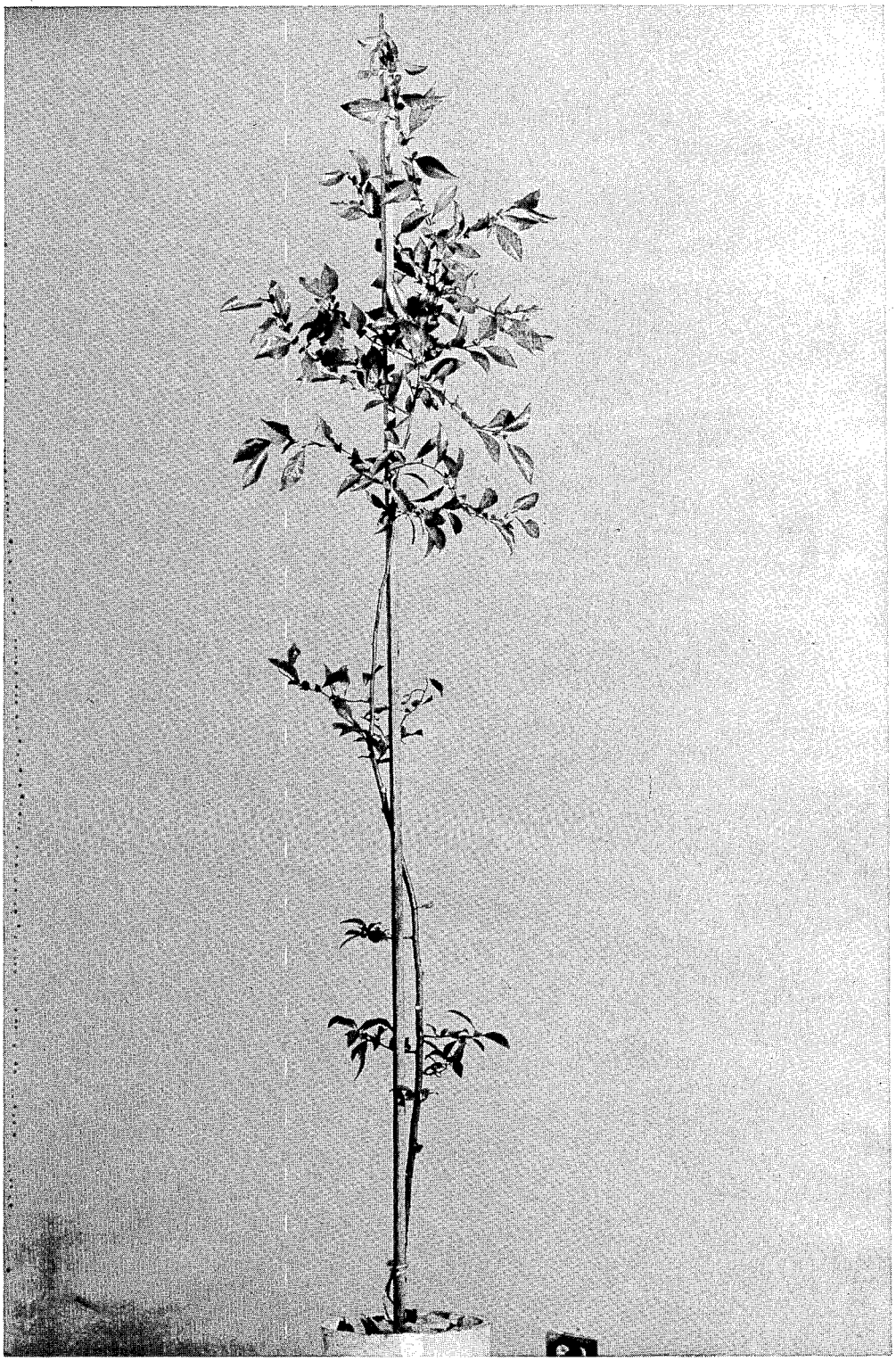
Inventor.
Jack R. Voeller.

United States Patent Office

Plant Pat. 2,422
Patented July 14, 1964

2,422
*CHAENOMELES LAGENARIA* CLIMBER

Jack R. Voeller, Rte. 1, Box 111, Mountainburg, Ark.

Filed June 4, 1962, Ser. No. 200,006
1 Claim. (Cl. Plt.—64)

The present invention relates to a new and distinct variety of *Chaenomeles lagenaria,* a sport branch or cane that I discovered on a shrub plant of *Chaenomeles lagenaria* three years ago in my nursery located at Route 1, Mountainburg, Arkansas.

As a result of this discovery I am now in possession of a new variety of decorative plant which I call *Chaenomeles lagenaria* climber which is endowed with the unique combination of outstanding characteristics which distinguish the same from its parent as well as from all other varieties of which I am aware.

The parent plant of this sport is covered by the usual botanical description of Chaenomeles as follows: A firm leaved shrub with typically axillary spines with roundish rather slender twigs, irregular rounded homogeneous pale pith, alternate raised crescent shaped small leaf scars with three sometimes compound bundle-traces, small stipule-scars, ovoid small solitary sessile buds with two exposed scales, crenulate to serrate moderate-sized short-stalked leaves, rather large solitary deep red perfect epigynous polypetalous flowers and large, fragrant, many seeded orange pomes.

At the time of discovery of this sport branch the terminal or main branch was over six feet in length, with four side branches of various lengths up to nearly three feet, mature wood on the main terminal was four feet in length which indicated that it was last season's growth, while the balance of terminal, plus the side branches, were green wood or current season's growth. Of this fact I am positive for I have a habit of trimming back all of our nursery stock a few weeks after blooming period which was in May 1959 at time of discovery. This sport branch was certainly not in evidence at pruning time the previous year. By that I assume the average yearly growth of this new sport variety is about four feet and up of new wood per growing season. After a close scrutiny of this branch I discovered some very outstanding charactertistics, which are unique, and which distinguish the same from its parent as well as from all other varieties of which I am aware:

(1) The plant was totally unarmed, in other words the usual spines were absent while the parent plant had spines all up and down the branches.

(2) The terminal leader had entwined itself to some extent around the branches of the parent plant which indicated its desire to climb.

(3) This was in May 1959 and although *Chaenomeles lagenaria* always bloom in March at this latitude I noted that on this sport branch there were numerous clusters of flowers in bloom at so late a date. No seed pomes were in evidence and I later discovered that seed pomes drop off after they attain a size of ¼ inch in diameter.

(4) On parent plant of this sport branch I find that all flowers are large, solitary and deep red along its branches, while on this sport branch flowers appear in clusters of from three to seven to a bunch and are all about the size of flowers on parent plant.

(5) This sport branch practically went dormant during the months of August and September 1959 but new leaves appeared before the first of October 1959 together with a large number of bloom buds which burst into flowers by the middle of the same month. Further, the plant kept on blooming until the 22nd day of December 1959 at which time a heavy freeze destroyed the leaves and flowers.

(6) Both parent plant and sport branch lived through a cold period of 16 degrees below zero for three winters and also through a summer temperature as high as 104 degrees without any apparent harm.

(7) This sport branch of *Chaenomeles lagenaria* climber has been asexually reproduced in two different ways or methods. One way is by budding to rooted stock of parent plant. Another way is to root cuttings taken from sport branch. The accompanying drawing or illustration shows a plant made from a cutting, which cutting was rooted in my greenhouse at Mountainburg, Arkansas, in December 1960 and which is now about one and a half years old and nearly five feet in height at present time.

The place or locale of the asexual reproduction of this plant was at my nursery located at Route 1, Mountainburg, Arkansas.

I claim:

A new and distinct variety of *Chaenomeles lagenaria,* as herein shown and described, characterized particularly as to novelty by the unique combination of absence of spines, its tendency to climb, profuse flowers in clusters rather than solitary flowers, two blooming periods per season rather than only one per season, and vigorous and healthy habits of growth even at extreme temperature variations.

No references cited.